United States Patent [19]

Sugaar

[11] Patent Number: 4,670,386
[45] Date of Patent: Jun. 2, 1987

[54] CANCER TESTS USING TUMOR ANTIGEN GENERATED LYMPHOKINES AND COMPOSITIONS

[76] Inventor: Stephen Sugaar, Rte. 22, Canaan, N.Y. 12029

[21] Appl. No.: 554,925

[22] Filed: Nov. 25, 1983

Related U.S. Application Data

[63] Continuation-in-part of Ser. No. 254,291, Apr. 15, 1981, abandoned, which is a continuation-in-part of Ser. No. 152,535, May 23, 1980, Pat. No. 4,343,895, which is a continuation-in-part of Ser. No. 165,559, Jul. 3, 1980, abandoned, which is a continuation-in-part of Ser. No. 151,906, May 21, 1980, abandoned.

[51] Int. Cl.[4] .................. C12Q 1/02; C12P 21/00; C12N 13/00; C12N 11/04
[52] U.S. Cl. ...................................... 435/29; 435/68; 435/173; 435/182
[58] Field of Search ................... 435/617, 29, 68, 173, 435/182; 436/535, 543–546, 813, 829

[56] References Cited

PUBLICATIONS

Svit et al., Cancer Research, vol. 37 (1977), 3836-7.
Hamblin et al., Chem. Abstracts, vol. 89 (1978) 17136j.
Thompson et al., Chem. Abstracts, vol. 89 (1978) 144781v.
McCollester et al., Chem. Abstracts, vol. 93 (1980) 19533t.
Li et al., Nature, 267 (May 12, 1977) 163-5.
Sega et al., J. Natl. Cancer Inst. 61 (1980) 1001-6.
Marmor et al., Cancer, 43 (1979) 188-97.
Sugaar et al., Cancer 43 (1979) 767-83.

*Primary Examiner*—Christine M. Nucker
*Attorney, Agent, or Firm*—Frishauf, Holtz, Goodman & Woodward

[57] ABSTRACT

The present invention provides strongly antigenic tumor-specific substances (also cellular material containing said strongly antigenic tumor-specific substances) prepared by radiofrequency or microwave electromagnetic radiation, acting on cancer tissue or cancer cells of known pathohistologic character. Said substances and also cellular material containing said substances are characterized by such sensitizing antigenic qualities that when they are contacted with a composition of naturally cancer-sensitized lymphocytes taken from a host having pathohistologically related cancer, then said lymphocytes produce and exude lymphokine.

The invention further provides diagnostic tests for cancer and compositions which contain or utilize said strongly-antigenic cancer-specific substances.

8 Claims, No Drawings

CANCER TESTS USING TUMOR ANTIGEN GENERATED LYMPHOKINES AND COMPOSITIONS

BACKGROUND OF THE INVENTION

This is a Continuation-In-Part of application Ser. No. 254,291 filed Apr. 15, 1981 (now abandoned) which in turn is a Continuation-In-Part of (i) application Ser. No. 152,535 filed May 23, 1980 (now U.S. Pat. No. 4,343,895); and (ii) application Ser. No. 165,559 filed July 3, 1980 (now abandoned) which was a Continuation-In-Part of abandoned application Ser. No. 151,906 filed May 21, 1980.

The present invention provides novel methods for the preparation of strongly antigenic tumor-specific substances and cancer diagnostic methods utilizing said substances, and provides novel compositions.

It is known that several human cancers such as melanomas, long, breast or colon cancer possess weakly antigenic tumor-specific substances on the membranes of their composing tumor cells. With the usual extraction methods such tumor-specific antigens, sometimes referred to in the literature as TSTAs and herein referred to as "TSAs", prove to be even weaker antigens than when in their native association with amalignant tumor cells; see K. Sikora et al's article "Partial Purification of Tumor-Specific Transplantati Antigens from Methylcholantrene-Induced Murine Sarcomas by Immobilized Lectins", British J. Cancer 40:831–838 (1979).

There is a recent report on the sensitization of circulating lymphocytes of women with breast cancers to breast cancer TSAs; see Wm. Gm Ramey et al's article "Detection of Breast Tumor Antigen-Sensitive Circulating T-Lymphocytes by Antigen-Stimulated Active Rosette Formation," Cancer Research 39:4796–4801 (1979). This effect is assumed to be due to persistent release of breast TSAs of weak antigenicity into the breast cancer patient's circulation. circulation.

Melanoma extracts can interreact with other melanoma patients lymphocytes invitro but not with lymphocytes of other types of tumors. (U. W. Jehn et al. "In Vitro Lymphocyte Stimulation By A Soluble Antigen From Malignant Melanoma", New England J. of Medicine 283:329–333, 1970). Similarly, extracts from osteosarcomas can in vitro stimulate lymphocytes of other osteosarcoma patients but not lymphocytes of other cancer patients. (B. J. Gainor et al, "A Method of Immunological Assay in Human Osteosarcoma", Clinical Orthopedics and Related Research (Philadelphia) 111:83, 1975).

It is known that when lymphocytes sensitized by strong antigens, e.g., Bacillus Calmette-Guerin (BCG), recontact in vivo or in vitro the strong sensitizing antigen, macrophages present at the site of reaction may fuse and form multinucleated giant cells; see A. H. Warfel's article "Macrophage Fusion and Multinucleated Giant Cell Formation, Surface Morphology", Experimental & Molecular Pathology 28:163–176 (1978). TSAs so far obtained from cancer cells are, as noted, weak antigens and when weak TSAs are contacted wtih lymphocytes in the presence of macrophages, no macrophage fusion reaction occurs in vivo or in vitro.

Heating to hyperthermic temperatures, e.g., 41.5°–43.5° C., improves the inherently weak immunogenicity of cancer cells, but the immunological change produced by heat was found to be inferior to the similar, still ineffectual immunogenic changes produced by X-rays; see H. D. Suit et al's article "Immunogenicity of Tumor Cells Inactivated by Heat", Cancer Research 37:3836–3837 (1977). X-ray irradiation is also known to exert a similar limited effect on embryonic or fetal tissue antigens according to E. Sega et al, "Specific Blastogenic Response of Peripheral Blood Lymphocytes from Lung Cancer Patients to a Fetal Lung Antigen," Journal of the National Cancer Institute, Vol. 64, No. 5, pages 1001–1006 (1980). TSAs after the reported heating or X radiation while becoming somewhat more active than TSAs without heating are not sufficiently activated to produce specific histologic changes or participate in in-vitro reactions such as the macrophage fusion reaction.

All publications referred to in this specification are incorporated by this reference.

It is an object of the invention to produce compositions containing TSAs having strong antigenic activity and further to utilize such strongly antigenic TSAs in test methods for cancer and for therapeutic uses.

SUMMARY OF THE INVENTION

Strongly antigenic TSAs are generated in viable cancer tissue or cancer cells or cancer cell membranes derived from malignant cells (inclusive of cells of leukemic character) by high frequency electromagnetic radiations that produce cyclic, very rapid, alternating changes of polarity in dipolar molecular components of cancer cells. Such radiations can simultaneously heat the rapidly vibrating cell components unless the cells are cooled while irradiated. Such radiations can be followed by elution or extraction of the generated strongly antigenic TSAs. The cancer derived material which is being irradiated is controlled at temperatures above 22° C. and preferably above about 25° C., for example between about 42° C. and about 55° C., and more preferably between about 42° C. and 50° C. The time of applying electromagnetic radiation may vary dependent upon the energy input per unit of time. Utilizing the presently preferred radiofrequency electromagnetic radiation, or electromagnetic radiation by microwaves, radiation is preferably carried out for a period between about 20 and 180 minutes, and more preferably between about 30 and 90 minutes. Cut cancer tissue is irradiated in the form of tissue slices or aggregates of tumor cells or cell membranes isolated from cancer cells suspended in water medium. Such medium becomes enriched in TSAs exuding from cancer cells or cancer cell membranes irradiated with electromagnetic power.

Strongly antigenic TSAs can be extracted from cancer cell material irradiated with electromagnetic power by the use of various previously known extraction methods or modifcations of the same.

The molecular weight of TSAs of the present invention is between about 20,000 and 300,000 and preferably between about 25,000 and 150,000 dalton, and more preferably between about 28,000 to 75,000 dalton. Crude TSA extracts also contain histocompatibility antigens (HL-As) which, like the TSAs, are (i) derived from the membranes of tumor cells and (ii) contain in non-covalent binding beta-2-microglobulin. The TSA extracts containing compositions of the present invention may be preferably utilized when HL-As and their bound beta-2-globulin have been removed from the TSA extracts disclosed hereinafter.

Presently, the molecular composition of TSAs is unknown. The strength of TSA in extracts may be assessed by their protein content as determined by Lowry's method.

TSAs in aqueous suspension is a usable form of the strong antigenic tumor-derived substance of the present invention. Preferably, these are encapsulated. It is also possible to use tumor cell material or tumor cell membranes which have been irradiated by electromagnetic radiation as disclosed herein without extracting TSAs from their native cellular bindings as alternate antigens to extracted or eluted TSAs as reagents in diagnostic tests or for therapeutic uses.

The strongly antigenic TSA extracts may be encapsulated in lamellar liposome vesicles to further increase the antigenic effect of TSAs. Encapsulation can be carried out by using the method disclosed in G. Poste et al's article "Lipid Vesicles as a Carrier for Introducing Materials into Cultured Cells: Influence of Vesicle Lipid Composition on Mechanisms of Vesicle Incorporation into Cells", Proc. Nat'l. Acad. Sci. 73:1603 (1976) or following F. Sakai et al's procedure disclosed in "Association of Gross-Virus Associated Cell-Surface Antigen with Liposomes", British Journal of Cancer 41:227–235 (1980).

The strongly antigenic TSAs specific to the type of cancer cells or derived or extracted from the same, obtained by the present invention are characterized by their capacity when contacted with lymphocytes obtained from cancer patients with similar pathohistologic tumor type in the presence of ambient (nearby) macrophages to cause aggregation and fusion of macrophages.

Strongly antigenic, tumor type related TSA generated and contained in, or eluted or extracted from cells of malignant tumors, the primary site and histologic character of which are known, are tested for in vitro induction of lymphokine production by lymphocytes of cancer patients. If a patient's lymphocytes after having been contacted with strongly antigenic tumor cells or tumor antigens of histologically known tumor derivation, exude lymphokines that lead to aggregation and fusion of added macrophages or to formation of multinucleated giant cells, then the patient has cancer of similar type and/or histological character as the known cancer from which the specific cancer cell material or TSA extract used in the test was derived from.

Strongly antigenic TSAs have other utility than solely for use in the macrophage fusion test. They may be used in other tests to determine the presence of related cancer; for example, in the blood platelet aggregation test or in the cytofluorometric test discussed hereinafter. Strong TSAs also have therapeutic utility, particularly TSAs in isolated cancer cell membranes or encapsulated within liposomes when used for extracorporeal or parenteral immunologic activation of mononuclear cells of immunocompetent cancer patients:

The macrophage fusion test is analogous to the test reported by B. Galindo et al, "Fusion of Normal Rabbit Alveolar Macrophasge Induced by Supernatant Fluids from BCG-Sensitized Lymph Node Cells After Elicitation by Antigen", Infection and Immunity 9:212–216 (1974), who first used such test with non-tumor-derived strong sensitizer substances such as BCG. The result of this in vitro test is established by counting the fused macrophages and multicellular giant cell formation visible on microsopic examination. Such cell aggregations and fusion form by the joining of single macrophages under the influence of lymphokines that originate from sensitized lymphocytes triggered by strong, sensitizing, specific antigen to produce lymphokines.

The blood platelet aggregation test is analogous to the macrophage fusion test. This test was described by K. L. Lavelle et al ("Identification of a New Platelet Aggregating Factor Released by Sensitized Leucocytes", Clinical Immunology and Immunopathology 3: 492–502, 1975) and employs blood platelets instead of macrophages as aggregation indicator cells.

MATERIALS AND METHODS

Originally, malignant tumor tissue (well-differentiated human squamous cell cancer of the lung) has been irradiated with electromagnetic power to produce therein substances which are tumor-specific and which have strong antigenic activity. Such radiation was carried out by dielectric electromagnetic power at 13.56 MHz frequency at 0.25 to 1 watt per square centimeter of tumor for up to 90 minutes. There was a second 90-minute treatment under substantially the same conditions. Strongly antigenic TSAs were formed in the treated cancer that reacted with lung cancer-sensitized lymphocytes that released lymphokines which reacted with nearby macrophages causing fusion of single macrophage cells producing giant cells with multiple nuclei present in a single cytoplasm.

Radiofrequency radiation may be carried out by dielectric or by inductive electromagnetic radiation. Of necessity the radiofrequency wavelengths utilized in the U.S.A. are within wavelength ranges allocated by the United States Government.

Microwaves, another way of electromagnetic radiation, may also be used. The cycle frequency of radiofrequency radiation is in the order of tens of millions cyles or vibrations per second. The cycle frequency of microwaves is of the order of one or more billion cycles per second. Since each frequency cycle involves two changes in polarity and affects all dipolar molecular cellular components, the subcellular components of cancer cells are subjected to sustained very rapid electromagnetic impulses exerting an intrinsic effect or such. The intrinsic, non-thermal but antigenically potentiating effect on cells can be separated from intrinsic plus thermal effect of radiation by cooling the vessel enclosing the irradiated cancer cells, cell membranes, or TSA extracts.

As noted by J. W. Schereschewsky in "Biological Effects of Very High Frequency Electromagnetic Ratiation", RADIOLOGY, Vol. 20, pages 246–253 (1933), there may be differential action upon individual tissue components by the special frequency at which cellular components take up energy preferentially.

The use of radiofrequency treatments with disclosure of the mechanical details of an apparatus for such purpose was described by J. A. Dickson et al in "Tumor Eradication in the Rabbit by Radiofrequency Heating", published in Cancer Research 37:2162–2169 (1977).

The use of radiofrequency electromagnetic radiation for treating human tumors was disclosed in the article by S. Sugaar and H. H. LeVeen entitled "A Histopathologic Study of the Effects of Radiofrequency Thermotherapy on Malignant Tumors of the Lung", CANCER, Vol 43, pages 767–783 (1979); and by F. K. Storm et al in "Normal Tissue and Solid Tumor Effects of Hyperthermia in Animal Models and Clinical Trials", Cancer Research 39:2245 (1979). Microwave treatment of tumors was disclosed in J. Mendecki et al's article "Microwave-Induced Hyperthermia in Cancer Treatment: Apparatus and Preliminary Results", *International Journal of Radiation Oncology Biology and Physics,* Vol. 4, pages 1095–1103 (1978); and in Raymond U et al's article "Microwave-Induced Hyperthermia in Combination with Radio Therapy of Human Malignant Tumors", *CANCER,* Vol 45, pages 638–646 (1980).

Radiofrequency of microwave electromagnetic effects are capable to produce very rapid polarity changes in dipolar molecules of cancer cells, cancer cell membranes or TSAs derived from the same, which are productive of sufficiently strongly antigenic changes therein so that when such are in contact with lymphocytes sensitized by cancer of the same type and/or same histology, in the presence of macrophages, aggregation-and-fusion of macrophages occurs. The amount of the electromagnetic power required in each instance is dependent upon the energy source, the apparatus, the geometry and dielectric properties of the applicator and of the cancer tissue absorbing said power, and is determined empirically in each instance.

Human cancer-specific antigens can be derived from surgically removed malignant tumors, recently removed tumors at autopsy or from masses of in vitro cultured cancer cells.

For pilot studies, the first two sources may be adequate, for large-scale preparations in vitro cultured cancer cell lines are preferably employed.

We include in the following methods best adapted to generate strongly antigenic cancer cells and cancer cell membranes containing antigenic TSAs.

I. (a) With surgically excised, aseptically handled, cut cancer tissue, or such obtained from autopsied organs, one volume of tumor tissue (e.g. 30 grams) freed from connective and fatty tissue, visible necrotic tissue and blood is placed into a chemically inert plastic bottle containing 2 vols. (60 ml) RPMI-1640 sterile culture medium (ph 7.4); or (b) in vitro cultured masses (e.g. $1000 \times 10^6$ malignant cells) of cancer cells or (c) 1 volume of leukemic cells (e.g. $1000 \times 10^6$ malignant cells), in 1 volume sterile culture medium is placed into the plastic bottle; is exposed to electromagnetic radiofrequency or microwave power. Dielectric electromagnetic radiation is generated, e.g. at 13.56 MHz or 2450 MHz crystal controlled frequency by an apparatus capable of 300 watts of adjustable output power to provide radiation directed to a plastic bottle surrounded by an applicator and containing viable cancer tissue in an electrolyte, e.g., tissue culture medium containing protease inhibitor substance (0.1 mM phenyl-methyl sulphonyl fluoride, or epsilon-amminocaproic acid 0.25 mg/ml). Thermometry of the cancer tissue enclosed and radiated is effected by a telethermometer connected to thermistor probes inserted into the bottled tumor tissue. The maintained and controlled temperature is measurd and monitored during brief periods when radiation and mechanical shaking is, momentarily, stopped.

It is preferred to use a solid, electrolyte-filled, soft, flexible applicator bag on its operative surface enclosing the chemically inert plastic bottle containing the cancer tissue in RPMI-1640 culture medium. The bag-type applicator is electrically matched to the inserted tumor-containing plastic bottle, i.e., it is designed to minimize the reflection of electromagnetic radiation from the interface between the applicator and the bottle with its contents. It is usually necessary to match the applicator with a separate coaxial tuner by pressing the bag-type applicator against the plastic bottle containing the tumor-material to be heated-and-vibrated by radiofrequency power. This is effected by adjusting the tuner until the power reflected from the tumor is minimal in extent. Bagtype applicators preferably filled with sold dielectrics are preferred for the purpose. Electromagnetically generated power is transmitted from the amplifier to an impedance matching circuit and thence to two insulated coaxial cables firmly attaced to the outside of the applicator bag which is covered on its surface by absorbent material. The bottle enclosed wet tumor-tissue is maintained while suspended in the buffered tissue culture medium at controlled temperatures at not less than 22° and not more than 55° C., and for periods not less than 20 and not more than 180 minutes at one exposure. Soluble cancer cell eluate entering the buffer solution consequent to electromagnetic wave exposure is salvaged and concentrated for during radiation the watery culture medium becomes gradually enriched in TSAs issuing from irradiated cancer cell membranes. Such TSAs can be concentrated by the hollow fiber extraction method.

After irradiation with electromagnetic radiation, the wet tumor tissue is cut with scalpel and scissors and the finely cut tumor particles are strained through 40 and then 60 mesh metal screens. The tumor particles and cells are washed 3 times with sterile phosphate-buffered saline and are suspended in 40 ml of a hypotonic buffer (10 mM Tris HCl, pH 7.5, containing 0.1 mM phenylemethyl sulphonyl fluoride (PMSF) to inhibit endogenous protease activity. For chemical extraction and purification of TSAs, I prefer to use the method of K. Sikora et al, *Br. J. Cancer,* Vol. 40, pages 831–838 (1979), which includes the following steps:

A. Cancer Cell Membrane Isolation and Solubilization

The tumor particle and cell suspension is given 20 strokes in a Dounce homogenizer and spun at $108,000 \times g$ for 1 hr. at 4° C. in a swinging-bucket centrifuge on a layer of 45% sucrose. The membrane fraction layers on top of the sucrose and is collected, resuspended in 0.01M phosphate-buffered saline (PBS) and pelleted by centrifugation for 30 minutes at $108,000 \times g$. The pellet is broken by pipetting with a Pasteur pipette and dissolved in 2 ml of 1% deoxycholate (DOC) in 0.01M phosphate-buffered saline (PBS) containing 0.1 mM PMSF. After 2 hr. of gentle mixing at 4° C., 2 ml of 0.01M PBS is added, to bring the DOC concentration to 0.5%. This mixture is spun for 30 minutes at $108,000 \times g$ and the supernatant is harvested.

The supernatant is dialysed in Visking tubing 8-1/32 at 4° for 48 hrs with 3 changes in the dialysate (0.01M PBS and 0.1 mM PMSF). This is effective in removing most of the deoxycholate. Aliquots of dialysed cancer cell membrane extract can be stored for at least a month at $-20°$ C.

The dialysed supernate containing TSAs can be further purified by passing it rhough columns of Sepharose beads coupled to an immobilized lectin (wheat-germ-agglutinin). Wheat-germ-agglutinin in covalent coupling to columns of Sepharaose beads is efficient for glycoprotein separation and can be used in the presence of low concentrations of detergent.

Watery extracts containing TSAs and HLAs strained through such columns attach TSAs to the lectin on the beads but not the HLAs. This purifies TSAs by a rather simple one-step procedure.

B. Preparation of Wheat-Germ-Agglutinin Columns

Wheat-germ-agglutinin (obtaininable from Pharmacia Fine Chemicals, Piscataway, NJ) is coupled to cyanogenbromide-activated Sepharose 4B (Pharmacia Fine Chemicals). 2 grams of Sepharose 4B cyanogenativated gel is swollen and washed for 15 minutes in 500 ml 1 mM HCl on a sintered glass filter. 10–50 mg of wheat-germ-agglutinin are dissolved in 10 ml of the coupling buffer (0.1M $NaHCO_3$, 0.1M NaCl, pH 8.3), which includes 2% of N-acetylglucosamine.

The washed, swollen gel is added to the coupling buffer and mixed for 2 hr at room temperature (19° C.). Unbound material is washed away with coupling buffer and any remaining active groups are reacted with 1M ethanolamine (pH 8.0) for 1 hr. Three washing cycles are used to remove non-covalently absorbed protein, each cycle consisting of a wash at pH 4.0 (0.1M sodium acetate, 1.0M NaCl), followed by a wash in coupling buffer. This procedure produces the binding of 70–80% of the lectin to the Sepharose as estimated from the optical density at 280 nm (OD 280) of added and unbound lectin.

C. Elution of Purified TSA Extract 5 ml of washed lectin-coupled gel is loaded into a plastic syringe on top of a small piece of glass wool. The column is equilibrated with loading buffer (0.01M $NaHOP_4$, $10^{-5}M$ $CaCl_2$, $10^{-5}M$ $MnCl_2$, 0.1 mM PMSF, 0.85% NaCl, 0.2% DOC, pH 7.3) and run at 25° C. Solubilized cancer cell membrane extract freed from desoxycholate by dialysis is loaded in a 2 ml volume and allowed to equilibrate for 30 minutes. The column is then washed with loading buffer until no further protein (determined by OD 280 of the effluent) is detected. Three washings, containing unbound components, are pooled. The eluting buffer, containing 2% of N-acetylglucosamine is then run into the column.

After 30 minutes equilibration, the column is washed with eluting buffer and again the washings collected, pooled and then dialysed for 48 hrs against 0.01M PBS and cencentrated by vacuum dialysis. The dialysed purified solubilized TSA extract can be preserved in a watery medium, e.g., in RMPI-1640 tissue culture medium aliquots, and stored at −20° C. TSA can be quantitated in individual aliquots either by O. H. Lowry's protein determination method (*J. of Biol. Chem.* 193:265–709, 1971.)

II. Preparation of Cancer Cell Membranes With Strong Specific Antigenic Effect, Viable cancer cells derived from finely cut and finely sieved fresh, surgically removed viable human cancer, or vaible in vitro cultured human cancer cell masses of known pathohistologic definition, are washed 3× with sterile saline and then suspended in saline containing 0.1 mM phenyl-methylsulfonyl-fluoride. After standing for 15 minutes at room temperature and a final saline wash, the sedimented cancer cells and introduced into a watery medium consisting of 150 mM NaCl, 1.0 mM $CaCl_2$, 1.0 mM $MgCl_2$ and 50 mM sodium borate at pH 7.2, and adjusted to yield a final pellet of approximately 1.2 ml. Each pellet is next suspended in 5 ml 2.5 mM sodium borate and 0.2 mM EDTA at ph 9.6 and rapidly mixed with 200 ml of the same solution. After 10 min., during which the cells burst and surface membrane separation occurs, the extraction is stopped by adding sodium borate at pH 9.6 to a final concentration of 20 mM. The white gel, largely made up of precipitated nuclear material, is removed with a mesh, and centrifugation at 5000×g for 10 minutes concentrates the surface membrane ghosts. These are suspended in saline followed by centrifugation at 5,000 rpm for 10 min. The supernate was decanted and the pellet suspended in 20 ml saline followed by centrifugation at 5,000 rpm for 10 min. After decantation the pellets are washed three times with phosphate buffered (pH 7.4) culture medium RPMI-1640; and evenly suspended in 5 ml of this medium for storage in the refrigerator prior to use as antigens or liposome-encapsulated antigens in cancer tests.

III. Extraction of TSAs from radiofrequency power heated cancer tissue or equivalent microwave power or ultrasound heating can also be carried out by a modification of the Reisfeld and Kahan method, *Fed. Proc.*, Vol. 29, page 2034 (1970), wherein 3M KCl hypertonic salt is slowly added to the cell suspension for a 30 minute period to reach a final concentration of 3M. The extraction mixture is incubated at 4° C. for 16 hours with constant stirring. Insoluble cell constituents are sedimented by ultracentrifugation at 164,000×g for 50 minutes. The supernatant containing solubilized TSAs are concentrated by dialysis against 50% sucrose solution, and then dialysed against 200 volumes of 0.15M saline for 16 hours. Precipitates formed during concentration and dialysis are removed by centrifugation at 48,000×g. The supernatant containing TSAs and HLAs is diluted with 15 volumes phosphate buffered saline and is further purified by absorption on wheat-germ-agglutinin columns and eluted therefrom as described hereinbefore.

Human malignant tumors obtained at surgery or at autopsy represent limited sources for cancer cell extracts. To obtain larger amounts of human cancer cell derived TSAs of sufficient uniformity and in greater quantities, in vitro mass cultures of known tumor cell lines are necessary. Fermentors, and/or the cytogenerator disclosed by S. Graff and H. Moser, "New Interpretations in Cancer Biology," *Journal of the Hospital for Joint Diseases* 23:59–79 (1972), are usable for the purposes of culturing cancer cells in great numbers. The TSA extraction methods described in the foregoing are applicable to cancer cells grown in bulk in mass cultures.

The term "extracted from said cancer material" refers to TSAs of increased antigenic activity obtained from radiofrequency irradiated cancer material which contains cancer cell membranes. This may be expressly extracted by methods such as those disclosed herein. They may also be "extracted" merely by elution into the aqueous culture medium from the cancer cells or cell membranes during irradiation as noted hereinbefore.

Methods and Materials for Preparation of Liposomes Containing TSA

Lipid spherules referred to as liposomes have been known as carriers for aqueous interphased water materials since their initial description by A. D. Bankham et al, "Diffusion of Univalent Ions Across the Lamellae of Swollen Phospholipids", *Journal of Molecular Biology*, 13:238–252 (1965). More recent disclosures of encapsulation in liposomes are contained in papers by W. E. Magee et al, "The interaction of Cationic Liposomes Containing Entrapped Horseradish Peroxydase with Cells in Culture", *Journal of Cell. Biology*, 63:492–504 (1974); S. Sone et al, "Rat Alveolar Macrophages are Susceptible to Activation by Free and Liposome-Encapsulated Lymphokines", *Journal of Immunology*, 124:2197-2002 (1980); and F. Sakai et al, "Association of Gross Virus-Associated Cell-Surface Antigen with Liposomes", *British Journal of Cancer*, 41:227-235 (1980) or S. Frokjaer's et al's method: "Stability and Storage of Liposomes" in "Optimization of Drug Delivery" A. Benzon Symposium 17, Munkgaard, Copenhagen, 1982. The liposome composition accoring to Frokjaer's method when the watery part of the composite containing the cancerspecific antigen is enclosed in a lipid composition of distearylphosphatidylcholine and cholesterol in molar ratio 2:1, remains stable and keeps well for a long time when stored in human blood plasma. The long storage-life of such liposomes gives them a practical advantage over liposomes of lesser keeping quality.

Liposome particles are prepared by the dispersion of dried films of phospholipids in an aqueous phase and materials such as the TSAs which are contained in the aqueous phase become trapped between the bilayer lamellae of the lipid particles.

Sphingomyelin liposomes can be prepared by dissolving 50 mg. of sphingomyelin (highly purified, from bovine brain), 10 mg. cholesterol, and 6 mg. stearylamine in 18 ml chloroform, together with a small amount of methanol. The solution is divided among six 50 ml round-bottom flasks or three 100 ml round-bottom flasks, and the solvent is removed by flash evaporation on a rotary evaporator at room temperature. The flasks are flushed with $N_2$ and 0.3-0.5 ml of the aqueous suspension containing the extracted TSAs is added per flask.

An alternate method for preparing liposomes is taking egg phosphatidylcholine, beef brain phosphatidylserine and lysolecithin at mole ratios 4.95; 4.95:0.01, respectivelly, in a total weight of 66 mg. This is dissolved in 18 ml chloroform, together with a small amount of methanol. The solution is divided among six 50 ml round-bottom flasks and the solvent flash evaporated, the flasks flushed with $N_2$ and the aqueous phase containing TSAs added in 0.3-0.5 ml quantities to individual flasks.

The films are dislodged from the glass by the use of a Vortex-Genie mixer. Two or three glass beads may be added to aid in looseining the lipid film. The liposomes are removed from the flasks, and the flasks rinsed with a small amount of aqueous phase. The liposomes are treated with ultrasonic vibration in intermittent 20 sec intervals at 4°-10° C. for a total of 1-2 minutes with a Branson Biosonic III vibrator equipped with a microprobe. The preparation is diluted with a saline-phosphate (0.15M NaCl and 0.01M phosphate, pH 6.9) and the liposomes collected by centrifugation at 60,000×g. for 30 minutes in the 50 Ti rotor of a Beckman Ultracentrifuge. The pelleted liposomes are resuspended and washed twice more by centrifugation and stored at 0°-5° C. suspended in salinephosphate for use in variable aliquots in the cancer tests.

Macrophage Fusion Assay

A. The macrophages utilized are pulmonary alveolar macrophages obtained from laboratory animals, preferably from rabbits. The preparation method follows the procedure described in Q. N. Myrvik et al's article "Studies on Pulmonary Alveolar Macrophages from the Normal Rabbit", *J. of Immunology* 86:123-132 (1961). Normal adult rabbits are sacrificed by injection of 4 ml veterinary Nembutal i.v. The thoracic cavity is opened and the trachea cannulated, introducing 40 ml isotonic tissue culture fluid into the pulmonary bronchial tree. The entry of blood into the operative area is carefully prevented; the lavage fluid is withdrawn from the lung and centrifuged at 1500 rpm for 20 minutes; aliquots of the sedimented alveolar macrophages are tested for viability by staining with 0.02% trypan blue solution. Viable macrophages are suspended in RPMI-1640 without serum, washed twice and recovered after centrifugation at 2,000×g for 10 minutes. Macrophage suspensions in culture medium are counted in hemocytometers and their concentration adjusted to $9 \times 10^6$ cells/ml.

B. Lymphocytes of cancer patients and other being tested for cancer are obtained by venipuncture. From 15 ml of heparinized or defibrinated blood of cancer patients and other persons, mononuclear cells are separated by A. Boyum's method using a ficoll-hypaque solution with a density of 1.076. Having pipetted off the interface cells, which are kept, the underlaying ficoll-hypaque solution is discarded. The erythrocyte pellet fraction is resuspended in medium in a volume equal to the volume of blood initially layered onto the gradient. To recover lymphocytes, this pellet function is pipetted on top of a fresh ficollhypaque gradient (density 1.083) and centrifuged at 750 g for 25 minutes at room temperature.

The cells of the interface fraction from the original 1.076 flotation layer and the interface fraction recovered from the second 1.083 ficoll-hypaque flotation layer are joined together and washed twice with RPMI-1640 culture medium. The sedimented lymphocytes are suspended in 30 ml of RPMI medium containing 10% heat-inactiviated human serum.

The monocytes present are removed by incubating the cell suspension in 75 $cm^2$ culture flasks (Falcon Plastics No. 3024) for 30 minutes at 37° C. Monocytes attach to tissue culture plastic surface and the lymphocytes are washed off by rinsing with 30 ml. culture medium.

After testing lumphocyte viability with the trypanblue exclusion test, aliquots of $10^6$ lymphocytes/ml are suspended in RPMI-1640 culture medium supplemented with 15% normal human serum, 0.1 mM 1-glutamine, 40 micro-gram gentamicin and 2-mercaptoethanol in 60 micromolar concentration.

Individual lymphocyte samples in round bottomed, screw capped 16×100 mm glass tubes (Kimax 45066, Kimble Prod., Toledo, Ohio, USA) in aliquots of 1 ml are cultured in 5% $CO_2$ humidified atmosphere at 37° C. for 24 hours with additions of 3 to 15 to 25 microgram TSA/ml or with 0.5 mo aliquots of evenly suspended cancer cell membranes/(ghosts)/ml prepared as previously described on page 15. After 24 hours, the tubes are centrifuged (500×g) and the cell-free supernatant removed and replaced by 1 ml fresh culture medium of the same composition and the incubation is continued for another 48 hours. The supernate is then aspirated, filtered through 0.22 micron Millipore filters and, if not used immediately, stored at 4° C.

C. Harvesting of normal alveolar macrophages

Healthy, nonsensitized rabbits are sacrificed, and their alveolar macrophages are procured by lavage. The alveolar macrophages were washed twice in RPmI-1640 medium without serum and recovered by centrifugation at 200×g for 10 min. The macrophage cell suspensions are counted with a hemocytometer chamber and adjusted to a concentration of $9 \times 10^6$ macrophage cells/ml.

0.5 aliquots of the aforesaid millipoer filtered cell culture supernate are placed separately into Wasserman tubes. A 0.1 ml sample of rabbit alveolar macrophage suspension ($1.5 \times 10^5$ cells) is added to each Wasserman tube. The resulting cell suspensions are dispensed into five wells of no. 3034 microtest tissue culture plates (Falcon Plastics, Oxnard, California). The plates are incubated under aseptic conditions in a $CO_2$ incubator (95% air, 5% $CO_2$) at 37° C. in humidified atmosphere and inspected for fusion of macrophages after 24 hours and at intervals thereafter up to 72 hours. Alternately, the lymphocyte response to antigens may be enhanced by culturing at 40° C., as disclosed in J. B. Smith et al's article "Human Lymphocyte Responses are Enhanced by Culture at 40° C. " *The Journal of Immunology*, Vol. 121, No. 2, pages 691–694 (1978). Routinely, incubation should be maintained for at least 24 hours (but incubations up to 72 hours should occasionally be employed). In positive cultures, there are fushed macrophages or multinucleated giant cells present at 24 hours incubation at the bottom of the culture wells. The number of single macrophages at 1 hour culturing and at 24 hours, as well as the number of fused macrophages, or giant cells (with nuclei in excess of 5 nuclei per cell) are counted and photographed at 100× magnification. The ratios and respective numbers of single and fused macrophage cells as well as the ratios of single and giant cells are recorded.

More than 30% fused macrophages including multi-nucleated giant cells present at 24 hours incubation are considered strongly positive (3+) results. Tests with less than 10% fused macrophages are considered 1+. Cultures containing 10% to 30% fused macrophages including multinucleated giant cells are considered 2+. However, the presence of any number of multinucleated giant cells is a positive finding for cancer of similar tumor type of histology to the TSAs used in test to which the patient's lymphocytes responded by producing lymphokines that fused added macrophages.

Alternately, it is possible to place macrophage cells in a watery suspension and add watery solutions of presumed lymphokines to the cell suspensions and follow and quantitate the rate and textent of eventual aggregation of macrophages in such media by using the aggregometer-test method described by B. Rouveix et al ("A sensitive technique for measuring specific macrophage aggregation" *Immunology*, 36; 589–594, 1979). Another aggregometric quantitative method testing for presence or absence of lymphokines generated upon exposure of sensitized blood platelets to sensitizing antigen in watery medium was described by K. J. Lavelle et al ("Identification of a New Platelet aggregating Factor Released by Sensitized Leucocytes", *Clinical Immunology and Immunopathology*, 3: 492–502, 1975).

The aggregometric methods of Rouveix et al, or, Lavelle et al are preferable to the original visual method used in the study of macrophage fusion reactions by B. Galindo et al: "Infection and Immunity" 9: 212–216, 1974.

Cytofluorometric Test

The presence of cancer sensitized lymphocytes in the peripheral blood taken from cancer patients can be determined using cytofluorometric analysis and more specifically by flow cytofluorometry. The degree of lymphocyte stimulation by tumor TSAs is detected by the result of the method disclosed by Braunstein et al, "Quantitation of Transformed Lymphocytes by Flow Cytofluorimetry," *Federation Proceedings*, Vol. 34, No. 3 (1975), as follows: Mononuclear cells separated from human peripheral blood by combined fractions obtained by Ficoll-Hypaque gradients as aforesaid are incubated at 37° C. or at 40° C. in 5% $CO_2$ atmosphere in RPMI-1640 containing 20 mM HEPES buffer and 10% normal human serum and 20 mM 1-glutamine at a cell concentration of 100,000 cells/ml. in the presence of TSAs in various (0.1 to 100 microgram) amounts. The samples are harvested at intervals up to 72 hours, fixed in 1:1 ethanol/acetone and stained with $10^{-5}$ g/ml acridine orange in a pH 6 buffer. Cytofluorimetric measurements (cytofluorograf 4801 interfaced to Nova 1220 minicomputer) on replicate samples of stimulated cells show increased per cell red fluorescence. The percentage of transformed cells is determined by quantitating the number of cells with fluorescence intensity falling outside the locus of unstimulated lymphocytes. The percentages of stimulated cells increases with time and varies with the individual, optimal sensitizer dose of TSAs. Fluorescence intensity higher than that of non-responding cells indicates a positive test for cancer related to type of cancer and/or histologic character of cancer to that of TSAs used as sensitizers.

The cancer tests disclosed herein indicate whether or not the lymphocytes used in the tests were derived from a person who currently has a malignant tumor or has had in the past cancer of such type or histologic character as the TSA used in the cancer test.

Compositions containing strongly antigen tumor-specific substances may be employed by extracorporeal or parenteral activation of small and/or large mononuclear cells of immunocompetent human cancer patients.

I claim:

1. A process of forming strongly-antigenic tumor-specific substances in viable human cancer-tissue, cancer cells or cancer cell membranes in vitro by positioning such in radiofrequency or microwave radiation fields that causes changes of alignment of electric charges in all polar cellular components of said cancer tissue or cancer cells or cancer cell membranes at the very rapid rate of electric field changes in said radiation fields following which in said cancer tissue or cancer cells or cancer cell membranes strongly antigenic tumor-specific substances are formed.

2. Water-soluble extracts or water-soluble eluates removed or issuing forth, respectively, from cancer tissue or cancer cells produced by the process of claim 1.

3. A process according to claim 1 wherein said radiofrequency or microwave electromagnetic radiation is carried out by inductive or dielectric method.

4. A process for the formation and secretion of lymphokine by viable, in vitro cultured lymphocytes, taken from an individual having cancer comprising and exposing said lymphocytes to and culturing together in vitro in an aqueous cell-culture medium with eluate or extract from cancer tissue of claim 2 or irradiated cancer cells submitted to the process forming strongly-antigenic tumor-specific substances according to claim 1, when said cancer tissue or cancer cells are identical or related in pathohistological character to the cancer of said individual.

5. The process of claim 4 wherein said culturing is carried out for 24 to 72 hours at 37° C. in germ-free condition in an atmosphere of 5% carbon dioxide in air, said culturing leading to secretion of lymphokine by lymphocytes.

6. Thin lipid layers of liposomes enclosing a water phase containing extracts or eluates of claim 2.

7. A laboratory diagnostic method for pathohistologically well-characterized forms of cancer comprising obtaining value lymphocytes from an individual tested for cancer of a definite pathohistological character,
    contacting said viable lymphocytes in a watery culture medium with cancer cells produced by the process of claim 1 or eluate or extracts of cancer cells of claim 2, said cancer cells being of identical or related pathohistological character to the cancer for which said individual is being tested to form watery composites, and
    culturing for 24 to 72 hours in vitro said watery composites in germ-free condition in a humid atmosphere containing 5% carbon dioxide in air,
    whereupon secretion of lymphokine by said lymphocytes is a positive diagnostic sign for cancer of said pathohistological character affecting said individual.

8. A laboratory diagnostic method for well-characterized forms of cancer comprising obtaining viable lymphocytes from an individual being tested for cancer of a definite pathohistological character,
    contacting said viable lymphocytes in a watery culture medium with liposomes comprising thin lipid layers enclosing a watery phase containing eluate or cancer cell extract produced according to claim 2 said cancer cells being of identical or related in pathohistological character to the cancer for which said individual is tested forming watery composites and
    culturing in vitro said watery composites for 24 to 72 hours in germ-free condition in a humid atmosphere containing 5% carbon dioxide in air,
    whereupon if said culturing leads to secretion of lymphokine from said lymphocytes, said individual has cancer of identical or related character as the pathohistologically known tumor-specific antigenic substance present in said liposomes watery phase.

* * * * *